(12) United States Patent
Hendl et al.

(10) Patent No.: US 7,659,061 B2
(45) Date of Patent: Feb. 9, 2010

(54) PHARMACEUTICAL COMPOSITIONS HAVING A MODIFIED VEHICLE

(75) Inventors: Ondrej Hendl, Portage, MI (US); Susan Marie Machkovech, Mattawan, MI (US); Niki Ann Waldron, Kalamazoo, MI (US); Nancy Jean Britten, Portage, MI (US); Dannette M. Shaw, Hopkins, MI (US); Alanta Lea Lary, Kalamazoo, MI (US); Thomas J. Yellig, Gobles, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 606 days.

(21) Appl. No.: 10/706,255

(22) Filed: Nov. 12, 2003

(65) Prior Publication Data

US 2004/0170650 A1 Sep. 2, 2004

Related U.S. Application Data

(60) Provisional application No. 60/427,680, filed on Nov. 19, 2002.

(51) Int. Cl.
*A61K 39/12* (2006.01)
(52) U.S. Cl. ........................................ 435/6; 424/204.1
(58) Field of Classification Search ........................ None
See application file for complete search history.

(56) References Cited

U.S. PATENT DOCUMENTS

| 4,297,353 | A |   | 10/1981 | Maulding | 424/247 |
| 5,013,713 | A | * | 5/1991  | Mitchell | 514/2 |
| 5,019,395 | A |   | 5/1991  | Mahjour et al. | 424/449 |
| 5,162,057 | A |   | 11/1992 | Akiyama et al. | 106/243 |
| 5,721,359 | A | * | 2/1998  | Dunn et al. | 540/227 |
| 5,736,151 | A | * | 4/1998  | Foster et al. | 424/423 |
| 5,739,159 | A |   | 4/1998  | Wolf | 514/475 |
| 6,074,657 | A | * | 6/2000  | Brown | 424/423 |
| 2002/0068065 | A1 |   | 6/2002  | Hendl et al. | 424/184.1 |
| 2002/0110561 | A1 | * | 8/2002  | Teagarden et al. | 424/147.1 |

FOREIGN PATENT DOCUMENTS

| WO | WO 94/00105    | 1/1994 |
| WO | WO 94/20505 A  | 9/1994 |
| WO | WO 96/20698    | 7/1996 |
| WO | WO 97/49402    | 12/1997 |
| WO | WO 98/41207    | 9/1998 |
| WO | WO 02/22107 A  | 3/2002 |

OTHER PUBLICATIONS

Fox and Stachowiak, "Vegetable oil-based lubricants—A review of oxidation", Tribology International, 40:1035-1046, 2007.
Adhvaryu et al., "Oxidation kinetic studies of oils derived from unmodified and genetically modified vegetables using pressurized differential scanning calorimetry and nuclear magnetic reasonance spectroscopy", Thermochimica Acta, 364:87-97, 2000.
Matheson Tri-Gas, Inc., Ethylene Oxide MSDS. Downloaded Dec. 22, 2006, from http://www.thesonitrogas.com/pdfs/msds/MAT09520.pdf.
Remington: The Science and Practice of Pharmacy, 20th Edition, Editors: Gennaro et al., p. 765, 2000.

* cited by examiner

*Primary Examiner*—Christopher R. Tate
*Assistant Examiner*—Roy Teller
(74) *Attorney, Agent, or Firm*—John H. Engelmann; Ludy X. Yang

(57) ABSTRACT

A composition comprising:
(a) one to three bioactive agents; and
(b) a vehicle comprising;
(i) a modified liquid carrier, and
(ii) an unmodified liquid carrier
wherein the ratio by volume of the modified liquid carrier to the unmodified liquid carrier is between 0.00001:99.99999 to less than 0.01:99.99, that provide the composition with predictable sustained-release properties and wherein immediately after manufacture of the composition, said composition can be administered to a host such that the one to three bioactive agents is released to the host on a sustained basis.

10 Claims, 2 Drawing Sheets

PHARMACEUTICAL COMPOSITIONS HAVING A MODIFIED VEHICLE

CROSS REFERENCE

This application claims the benefit of the following provisional application: U.S. Ser. No. 60/427,680, filed 19 Nov. 2002 under 35 USC 119(e)(i), which is incorporated herein by reference in its entirety.

BACKGROUND OF THE INVENTION

1. Field of the Invention

The present invention relates to pharmaceutical compositions. More specifically, it relates to the use of pharmaceutically acceptable vehicles comprised of (i) a modified liquid carrier and (ii) an unmodified carrier, wherein the ratio by volume of the modified liquid carrier to the essentially un-oxidizable carrier is between 0.00001:99.99999 to less than 0.01:99.99, that provide the composition with predictable sustained-release properties.

2. Background of the Invention

In the pharmaceutical arts, drug delivery is an element as significant as drug activity. Many drugs or bioactive agents with apparent in vitro activity fail at the clinical level due to the inability to prepare, store, or deliver the bioactive agent to the site of action in effective concentrations over a sufficient period of time.

A vehicle for the stable storage and effective delivery profile of a bioactive agent is of great utility. Those skilled in the art will understand that storage stability and effective delivery profile are, to some extent, specific to bioactive agents, the condition for which the bioactive agent is administered, and the presenting condition of the subject.

Sustained-release or oil-based preparations are considered in WO 97/49402 (Vlaminck); WO 94/00105 (Sabater); U.S. Pat. No. 4,297,353 (Hawkins); U.S. Pat. No. 5,019,395 (Mahjour); U.S. Pat. No. 5,739,159 (Wolf); U.S. Pat. No. 5,162,057 (Akiyama); WO 96/20698 (Levy); the teachings of which are incorporated herein by reference. Also incorporated by reference is WO 98/41207 (Brown) addressing subcutaneous administration of antibiotic into the ear of an animal.

U.S. Pat. No. 5,721,359 discloses the molecule crystalline ceftiofur free acid (CCFA), which is a cephalosporin antibiotic intended for use in mammals, and in particular food animals (e.g., cattle, sheep, goats and swine). The patent suggests that oil suspensions of CCFA can be produced for administration to food animals where the oils are vegetable oils. The oils as disclosed in the patent are intended to be used in their natural form. An advantage of this molecule over other antibiotics, particularly those in the ceftiofur family, is that it can be used to prepare a sustained-release pharmaceutical composition. However, the sustained release profile of formulations described in U.S. Pat. No. 5,721,359 is not readily predictable and reproducible with respect to the release of active drug in the immediate post-production product that uses natural vegetable oils. U.S. patent application 2002/0110561 discloses sustained release formulations comprised of a) a modified liquid carrier and b) an essentially un-oxidizable carrier, wherein the ratio by volume of the modified liquid carrier to the essentially un-oxidizable carrier is between 0.01:99.99 to 90:10 that provide the composition with predictable sustained-release properties.

Despite the above teachings, there still exists a need in the art for pharmaceutical compositions that provide sustained-release delivery of a bioactive substance and wherein the release performance is predictable and reproducible immediately after manufacture of the product.

BRIEF SUMMARY OF THE INVENTION

Surprisingly, we have found that a composition comprising:
  (a) one to three bioactive agents; and
  (b) a vehicle comprising:
    (i) a modified liquid carrier, and
    (ii) an unmodified liquid carrier provides the desired release performance characteristics with a ratio by volume of modified liquid carrier to un-oxidizable carrier as low as 0.00001:99.99999. Thus, the present invention provides a novel pharmaceutical composition that provides sustained-release of a bioactive component and wherein the release performance is predictable immediately after manufacture of the product. More specifically, the predictable performance is obtained by using a modified liquid carrier in very low proportion to the un-oxidizable carrier.

One embodiment of the invention provides a pharmaceutical composition comprising:
  (a) one to three bioactive agents; and
  (b) a vehicle comprising:
    (i) a modified liquid carrier, and
    (ii) an unmodified liquid carrier wherein the ratio by volume of the modified liquid carrier to the unmodified liquid carrier is 0.00001:99.99999 to less than 0.01:99.99, and wherein immediately after manufacture of the composition, said composition can be administered to a host such that there is sustained-release one to three bioactive agents.

In another embodiment, the bioactive substance is CCFA and the modified liquid carrier of the vehicle is a modified unsaturated oil such as modified cottonseed oil and the unmodified liquid carrier is a natural fully saturated oil such as saturated coconut oil.

A further embodiment of the present invention provides a method for producing a pharmaceutical composition comprising the step of modifying a liquid carrier and combining said modified liquid carrier with an unmodified liquid carrier to provide a vehicle. The vehicle is then combined with a bioactive substance to provide the pharmaceutical composition. According to this method the unsaturated oil is modified by the use of chemical, physical or mechanical means, or combinations thereof, to produce a carrier that has a higher level of oxidation products as compared to its original, or un-modified form. One embodiment of the method comprises the use of a combination of heat and gamma radiation. In addition, the modification step of this process may occur either prior to, after or both prior to and after the combining step.

A more specific aspect of this method comprises the steps of:
  (a) heating natural cottonseed oil or trilinolein in the presence of air to increase its oxidation products and yield a modified cottonseed oil;
  (b) combining said modified oil with saturated coconut oil or saturated coconut oil products to yield a carrier vehicle wherein the ratio by volume of the modified oil to saturated coconut oil is between 0.00001:99.99999 to less than 0.01:99.99;
  (c) adding crystalline ceftiofur free acid to said carrier vehicle; and, optionally, thereafter;
  (d) heating said pharmaceutical composition;
  (e) cooling said composition;

(f) filling one or more vials with said composition; and (g) exposing said one or more vials to gamma radiation.

Non-limiting examples of ratios by volume of modified carrier to un-oxidizable carrier of less than 0.01:99.99 are 0.0095:99.9905, 0.0090:99.9910 and 0.001: 99.999.

A further embodiment of the present invention provides the composition of the present invention for use in medical treatment of animals in need of treatment.

An additional embodiment of the present invention provides the use of the inventive composition to prepare a medicament for treating or preventing a disease in an animal, including humans.

Another embodiment of the present invention provides a method of treating or preventing a disease comprising administering to an animal in need of such treatment an effective amount of the inventive composition. One aspect of this invention is the treatment of bacterial infections in animals, including food animals, with an inventive CCFA composition.

An object of the present invention is to provide a novel composition that provides sustained release of a bioactive substance.

Still another object of the present invention is to provide a method for producing a novel composition that provides sustained release of a bioactive substance.

A further object of the present invention is to provide a method for treating a disease or condition in an animal in need of such treatment.

These, and other objects, will readily be apparent to those skilled in the art as reference is made to the drawings and detailed description of the preferred embodiment.

DETAILED DESCRIPTION OF THE INVENTION

Figure 1:
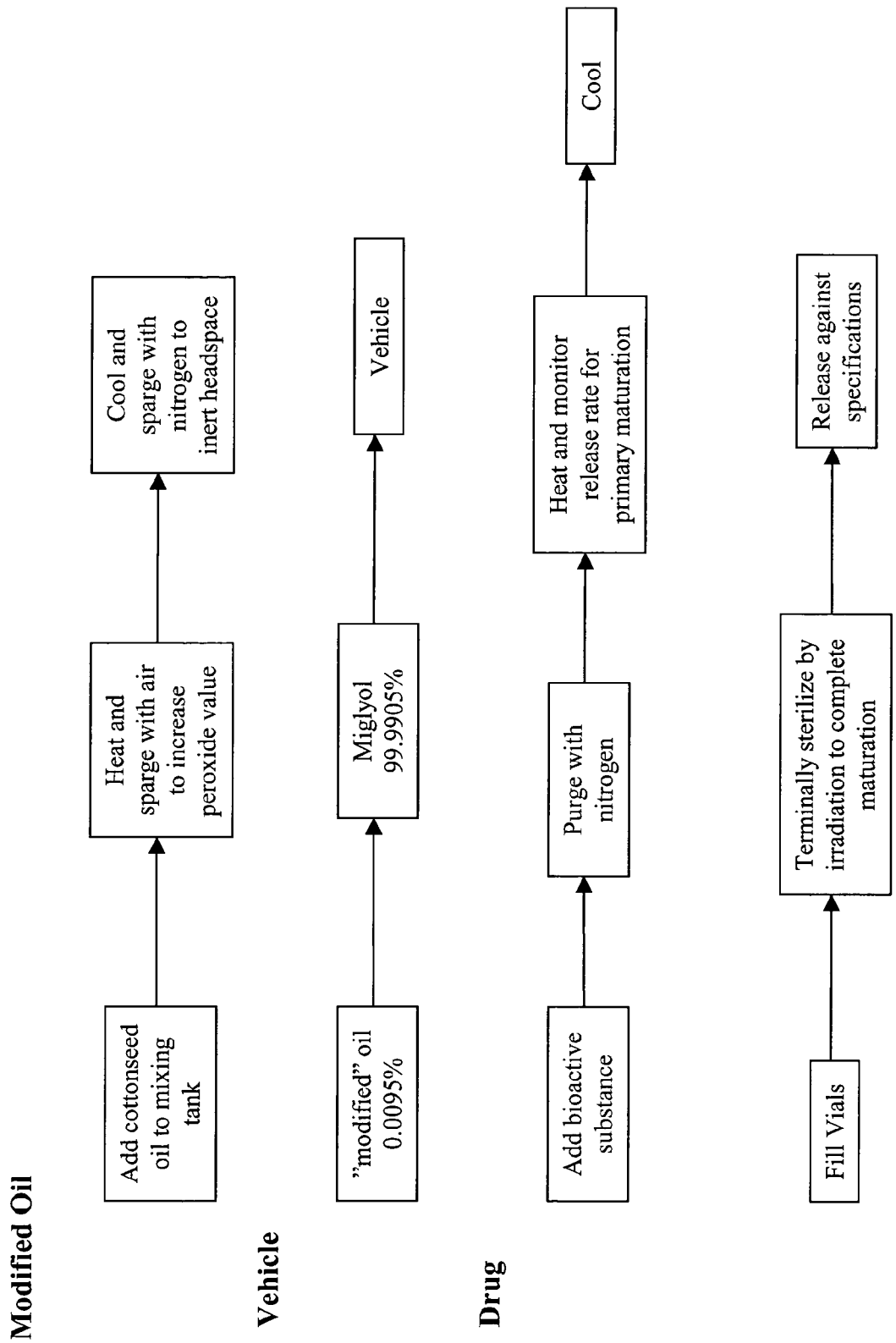
FIG. 1 is a diagram of a method that can be used to produce the inventive compositions.

In describing the preferred embodiment, certain terminology will be utilized for the sake of clarity. Such terminology is intended to encompass the recited embodiment, as well as all technical equivalents that operate in a similar manner for a similar purpose to achieve a similar result.

1. Terminology Definitions

This invention will be better understood with reference to the following definitions:

"Bioactive substances" shall be broadly understood to mean pharmaceuticals, immunogenic and immunomodulator compositions (including adjuvants), vectors such as liposomes and live vectors such as plasmids, viruses, spores, nutritional supplements and bacteria and mixtures thereof. These include, but are not limited to nutritional supplements, anti-infectives (e.g., antibiotics, antifungals, anti-virals), antineoplastics (e.g., anticancer agents, such as cis-platinum compounds), immunomodulators (e.g., antihistamines, immunoenhancers and immunosupressors), laxatives, vitamins, decongestants, gastrointestinal sedatives, antacids, anti-inflammatory substances, anti-manics, vasodilators (coronary, cerebral and peripheral), psychotropics, narcotics, stimulants, anti-diarrheal preparations, anti-anginal drugs, analgesics, anti-pyretics, hypnotics, sedatives, anti-emetics, growth promoters, anti-nauseants, anti-convulsants, neuromuscular drugs, hyper and hypo glycemic agents, thyroid and anti-thyroid preparations, diuretics, cytotoxic compounds, anti-spasmodics, anti-arthritics, uterine relaxants, anti-obesity drugs, anthelmintics, hormones, vaccines, mineral and nutritional additives, CNS agents not disclosed in this listing and any mixtures thereof. Specifically preferred bioactive agents include, but are not limited to, ceftiofur, including crystalline ceftiofur free acid (CCFA), platinum compounds (e.g., cis-platinum), ibuprofen, piroxicam, 1-[2-(4-fluorobenzoyl)aminoethyl]-4-(7-methoxynaphthyl) piperazine hydrochloride (FAMP), camptothecin, paclitaxel, flucytosine, cyclooxygenase-II inhibitors (e.g., coxibs and chromenes) and quinine.

"Sustained-delivery or Sustained-release" as used in relation to bioactive substances shall mean continued release or distribution of the bioactive substance such that the amount of bioactive substance remains in a patient's blood levels at a concentration of greater than a value that produces therapeutically effective blood levels of active substance(s) over an extended period of time. The effective sustained-release blood levels desired differ depending on the bioactive substance, the disease being treated, the patient, and the like, is considered to be known to the skilled practitioner and can be determined by routine experimentation. If, for example, the bioactive substance is ceftiofur crystalline free acid (CCFA), the desired level of ceftiofur metabolites in the patient's blood plasma needs be maintained at or above 0.2 μg/ml for effective treatment. In one embodiment of the invention, a single dose of sustaining-vehicle/CCFA maintains a ceftiofur metabolite level in the blood plasma of at or above 0.2 μg/ml for at least three and preferably four to five days post-administration. "Sustained-delivery" as used in this document is to be specifically reconciled with the regulatory definition for the same term that requires that the concentration versus time profile have three distinct phases (i.e., an increasing concentration phase, a plateau phase and a concentration depletion phase). While the term "sustained-delivery" as used in this document may encompass the above regulatory definition it is not intended to be limited to it as compositions that are sustained delivery as defined herein need not possess the three distinct phases (e.g., the composition may have an increasing concentration phase and an extended concentration depletion phase).

"Unsaturated oils suitable for modification" include unsaturated triglyceride fats and oils, including those derived from vegetable, animal, marine and synthetic sources. Examples of liquid carriers suitable for modification having unsaturated hydrocarbon side chains include, but are not limited to, naturally occurring oils such as castor oil, safflower oil, cottonseed oil, corn oil, olive oil, cod liver oil, almond oil, avocado oil, palm oil, sesame oil, peanut oil, and soybean oil. By way of example, cottonseed oil is available in a preparation of 70% unsaturated fatty acids (Sigma, St. Louis, Mo.). Synthetic oils that may be liquid carriers suitable for modification include glycerides, or propylene glycol di-esters of unsaturated fatty acids having from 6 to 24 carbon atoms. Examples of unsaturated carboxylic acids include oleic, linoleic, linolenic acid and the like. It is understood that the glyceride vehicle may include the mono-, di-, or triglyceryl ester of the fatty acids or mixed glycerides and/or propylene glycol di-esters wherein at least one hydroxyl of glycerol has been esterified with fatty acids of varying carbon atom length. Examples of tri-unsaturated triglyceryl esters are triolein and trilinolein. From di-saturated-mono-unsaturated: oleodisaturated are 1,2-dipalmitoyl-3-oleoyl-rac-glycerol or 1,3-dipalmitoyl-2-oleoyl-rac-glycerol and 1,3-dipalmitoyl-2-linoleoyl-rac-glycerol. Further examples of triglycerides are mono-saturated-di-unsaturated esters: mono-saturated-oleolinolein esters are 1-Palmitoyl-2-oleoyl-3-linoleoyl-rac-glycerol and 1-linoleoyl-2-oleoyl-3-stearoyl-rac-glycerol, mono-saturated-dilinolein is 1,2-dilinoleoyl-3-palmitoyl-rac-glycerol. Examples of diglyceryl esters: di-unsaturated esters are 1,2-diolein or 1,3-diolein, 1,2-dilinolein or 1,3-dilinolein and 1,2-dilinolenin or 1,3-dilinolenin, saturated di-saturated esters 1,2-dipalmitin or 1,3-dipalmiting, 1,2-distearin or 1,3-distearin, and 1,2-didecanoin or 1,3-didecanoin.

Non-limiting examples of saturated-unsaturated diglyceril esters include the tri-saturated esters tripalmitin, tristearin, and tridecanoin, 1-palmitoyl-2-oleoyl-glycerol or 1-oleoyl-2-palmitoyl-glycerol, 1-palmitoyl-2-linoleoyl-glycerol or 1-linoleoyl-2-palmitoyl-glycerol. Non-limiting examples of monoglyceryl esters: unsaturated esters are 1-olein or 2-olein, 1-linolein or 2-linolein and 1-linolenin or 2-linolenin. Non-limiting examples of polyethylene glycol (PEG) unsaturated di-esters include 1,2-diolein or 1,3-diolein, 1,2-dilinolein or 1,3-dilinolein and 1,2-dilinolenin or 1,3-dilinolenin. From saturated-unsaturated diglyceril esters: 1-palmitoyl-2-oleoyl-glycerol or 1-oleoyl-2-palmitoyl-glycerol, 1-palmitoyl-2-linoleoyl-glycerol and 1-linoleoyl-2-palmitoyl-glycerol.

The un-modified liquid carrier can be an unsaturated oil suitable for modification that has not been modified or an essentially un-oxidizable carrier. Examples of essentially un-oxidizable carrier include, but are not limited to, esters of medium to large chain saturated fatty acids (e.g., saturated fatty acid triglycerides with a chain length of about $C_6$ to about $C_{24}$). Non-limiting examples of saturated, essentially un-oxidizable oils include glycerol or propylene glycol esters of saturated fatty acids having from 6 to 24 carbon atoms such as hexanoic acid, octanoic (caprylic), nonanoic (pelargonic), decanoic (capric), undecanoic, lauric, tridecanoic, tetradecanoic (myristic), pentadecanoic, hexadecanoic (palmitic), heptadecanoic, ocatadecanoic (stearic), nonadecanoic, hexadecanoic (palmitic), heptadecanoic, eicosanoic, heneicosanoic, docosanoic and lignoceric acid. In some embodiments, about $C_8$ to about $C_{12}$ saturated fatty acid medium chain triglycerides (MCT) obtained from natural oils (e.g., coconut oil, palm kernel oil, babassu oil, etc.) are useful including those sold under the MIGLYOL trademark from Huls and bearing trade designations 810, 812, 829 and 840. Also noted are the NeoBeeRTM products sold by Drew Chemicals. Isopropyl myristate is another example of an un-oxidizable vehicle of the current invention. Non-limiting examples of polyethylene glycol (PEG) saturated di-esters include 1,2-dipalmitin or 1,3-dipalmitin, 1,2-distearin or 1,3-disteraearin, and 1,2-didecanoin or 1,3-didecanoin.

"Modified" and "modification" as to the vehicles of this invention and as used in the claims shall be understood to define an unsaturated vehicle which, through physical, chemical or mechanical means, has been altered as compared to its natural (or "unmodified" in the case of synthetic liquid carriers) form such that the modified vehicle has an increased level of oxidation products. Modification can be accomplished in the presence of an oxygen source by heat modification, irradiation and/or exposure to energy sources (e.g., light, ultraviolet, infrared, gamma, X-ray or microwave radiation), addition of catalysts (i.e., t-butyl peroxide), the incorporation of specific triglycerides and their hydroperoxides, incorporation of polymeric species, incorporation of crosslinkers or of polymerization causing agents, oxidation regimens and combinations of these methods. Suitable oxygen sources include, but limited by, air, oxygen, organic or inorganic peroxides and the like. These steps can be taken before or after addition of the drug to the vehicle, or both before and after addition of drug to the vehicle.

"Substantially peroxidized unsaturated oil vehicle" shall refer to a modified liquid carrier having a peroxide value of between 0.1 and 600, and in some embodiments 10, 20, 40, or 80 or any value in between. As used herein, peroxide values are expressed as milliequivalents (mEq) of peroxide per 1000 grams of oil sample. Peroxide value is conveniently measured by American Oil Chemists' Society (AOCS) (Official Method Cd 8-53)(Official Monographs, Soybean Oil, page 1434) manual titration, the teachings of which are incorporated herein by reference.

2. The Invention

The present invention comprises a composition comprising:
(a) one to three bioactive agents;
(b) a modified liquid carrier; and
(c) an essentially un-oxidizable carrier;

wherein the ratio by volume of the modified liquid carrier to the essentially un-oxidizable carrier is between 0.00001:99.99999 to less than 0.01:99.99 (v/v), and wherein immediately after manufacture of the composition, said composition can be administered to a host to provide sustained release of one to three bioactive agents.

It is a substantial advantage to identify a dosage form and method of preparation of a dosage form that provides sustained-release capability immediately upon production and maintains that release profile during a substantial storage period. In the present invention, a combination of preparatory steps and vehicle compositions are defined which yield sustained-release formulations upon processing. In all embodiments, a key feature is that a portion of the carrier vehicle has been modified either before, after or both before and after it has been combined with the bioactive agent.

The bioactive agents for use are as defined above. A preferred bioactive agent is crystalline ceftiofur free acid (CCFA) which is useful as an antibiotic drug compound in pharmaceutical dosage forms for treating valuable mammalian animals and humans suffering from bacterial infections. In particular embodiments, sustained-release ceftiofur free acid is useful as a veterinary antibiotic drug to treat animals such as cattle, swine, horses, sheep, goats, dogs, poultry and cats. Such treatment fights the effects of bacterial infections caused by susceptible organisms, such as *Pasteurella haemolytica* (Mannheimia Spp.), *Pasteurella multocida, Salmonella typhimurium, Salmonella choleraesuis, Actinobacillus pleuropneumoniae, Streptococcus suis, Streptococcus equi (zooepidemicus)*, and other *Streptococcus* bacteria, *Haemophilus somnus, Escherichia coli, Staphylococcus aureus* and the like, as well as applicable anaerobic infections, such as *Fusobacterium necrophorum*. These types of infections are commonly associated with diseases in animals, such as foot rot, bovine respiratory disease and swine respiratory disease.

In one example, the modified unsaturated oil comprises modified cottonseed oil and the un-oxidizable vehicle comprises saturated coconut oil or a saturated coconut oil product (for example MIGLYOL 812). So called "induced" cottonseed oil which has a higher level of oxidation products as a result of natural cottonseed oil having been heated in the presence of oxygen is specifically contemplated as being a type of modified cottonseed oil. When the bioactive agent is CCFA, it is preferably combined with this example vehicle such that the concentration of the CCFA in the composition ranges between 50 mg/ml to 250 mg/ml and usually between 100 mg/ml to 200 mg/ml. In another example, the modified oil is prepared from trilinolein.

FIG. 1 presents a useful processing scheme for producing a sustained-release product of this embodiment. Natural (unmodified) cottonseed oil is added to a mixing tank that is then heated and sparged with air to increase the peroxide value. The cottonseed oil is then cooled and sparged with nitrogen. The cottonseed oil at this point is deemed modified cottonseed oil. The vehicle is then prepared by mixing an appropriate amount by volume of modified cottonseed oil with an appropriate amount by volume of a saturated coconut oil or saturated coconut oil product, for example Miglyol 812, to produce a vehicle having a ratio of modified carrier to unmodified carrier of between 0.00001:99.99999 to less than 0.01:99.99. The bioactive substance, for example CCFA, is added to the vehicle and the mixture is purged with nitrogen. The purged mixture is heated and the release rate of the drug is monitored using an in process assay procedure to determine when the desired release rate is achieved. At this point the heating is terminated and the mixture is cooled, filled into vials and terminally sterilized by gamma irradiation and released against final specifications.

It is further contemplated that sustained-release formulations of other embodiments can be achieved by alternate routes within the disclosed process. For example, in one such process, drug is added to a mixture of an unmodified unsaturated oil and an essentially un-oxidizable oil and directly subjected to terminal irradiation to modify the unsaturated oil and produce a vehicle with sustained-release characteristics. In another, the process is terminated after fill and without terminal sterilization. In an embodiment consisting of mixture of a modified non-oil such as PEG 400 and an essentially un-oxidizable oil such as Miglyol 812, the drug/PEG-400/Miglyol 812 mixture is purged with nitrogen, heated, cooled and filled. It is an important aspect of the invention that not all processing steps are required to result in a composition with sustained-release characteristics in every protocol. However, in accordance with the present invention some type of chemical, physical, or mechanical modification or any combination of the above is required.

In addition to the instant inventive vehicle of the instant invention, the compositions of this invention can be employed in admixture with conventional excipients, i.e., pharmaceutically acceptable organic or inorganic carrier substances suitable for parenteral, enteral (e.g., oral or inhalation) or topical application which do not deleteriously react with the active compositions. Suitable pharmaceutically acceptable carriers include, but are not limited to, water, salt solutions, alcohols, gum arabic, vegetable oils, benzyl alcohols, polyethylene glycols, gelatin, carbohydrates such as lactose, amylose or starch, magnesium stearate, talc, silicic acid, viscous paraffin, perfume oil, fatty acid esters, hydroxy methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compositions. They can also be combined where desired with other active agents, e.g., vitamins. In specific embodiments, the liquid carrier may additionally contain a thickening agent, for example, beeswax, hard paraffin or cetyl alcohol. Also noted as optional additives are benzyl alcohols, polyethylene glycols, viscous paraffin, perfume oil, and fatty acid esters.

The inventive compositions are useful for human and veterinary medicine. More specifically, the compositions of the present invention can be used to treat humans, food animals or companion animals. This includes, but is not limited to, the following: food animals such as cattle, swine, sheep, goats and deer; companion animals such as horses, cats and dogs; poultry; or humans. The amount of inventive composition to be administered is that which will deliver the bioactive agent in an amount and for a duration to provide a therapeutic benefit necessary to treat or prevent a disease without causing toxicity problems to the patient. The specific amounts to be selected are deemed to be within the skill of the artisan. For example, when CCFA is selected as the bioactive agent, it is administered in unit dosage form for intramuscular or subcutaneous administration comprising about 0.5 to about 10.0 mg CCFA/kg body weight of patient with preferred ranges of about 4.4-6.6 mg/kg for cattle, and 5.0-7.5 mg/kg for swine. To the extent necessary for completion, the dosages as described in U.S. Pat. Nos. 5,721,359 and 6,074,657 are expressly incorporated by reference.

Administration of the composition is contemplated to include chronic, acute or intermittent regimens, and any mode where liquid administration is feasible may be selected. The compositions of the present invention can be administered parenterally (for example, subcutaneous, intramammary, intravenous, intraperitoneal or intramuscular injection), topically (including but not limited to surface treatment, transdermal application, and nasal application), intravaginally, orally, or rectally.

For oral therapeutic administration, the composition may be administered in the form of capsules, elixirs, suspensions, syrups, and the like. Such compositions and preparations should, typically, contain at least 0.1% of active compound. The percentage of the compositions and preparations may, of course, be varied and may conveniently be between 2 to about 60% of the weight of a given unit dosage form. The amount of active compound in such therapeutically useful compositions is such that an effective dosage level will be obtained. A syrup or elixir may contain the active compound, sucrose or fructose as a sweetening agent, methyl and propylparabens as preservatives, a dye and flavoring such as cherry or orange flavor.

Of course, any material used in preparing any unit dosage form should be pharmaceutically acceptable and substantially non-toxic in the amounts employed.

For parenteral application, the compositions can be administered intravenously or intraperitoneally, by infusion or injection. In one embodiment where CCFA is the bioactive agent, subcutaneous ear injection in accordance with U.S. Pat. No. 6,074,657 is an appropriate mode of administration. Intramuscular, intramammary and general subcutaneous administration is also specifically contemplated.

For topical administration, the composition may be applied in the form of drops (for example to treat diseases or infections of the eye), or for skin application in the form of spreadable pastes, gels, ointments, soaps, and the like. The resultant liquid compositions can additionally be applied from absorbent pads or suppositories, used to impregnate bandages and other dressings, or sprayed onto the affected area using pump-type or aerosol sprayers.

It will be appreciated that the actual preferred amounts of active compositions in a specific case will vary according to the specific compositions being utilized, the particular compositions formulated, the mode of application, and the particular situs and organism being treated. Dosages for a given host can be determined using conventional considerations, e.g., by customary comparison of the differential activities of the subject compositions and of a known agent, e.g., by means of an appropriate, conventional pharmacological protocol.

An important aspect of the present invention is that by performing the modification to the carrier vehicle, the in vivo performance of the bioactive substance can be entirely controlled and predictable. As such, the performance of the bioactive substance in vivo is comparable from the time of manufacture for many months of storage time. As an example, the performance of the bioactive agent administered in vivo 30 days, 60 days, 90 days, 180 days, 360 days or 720 days after manufacture is comparable to the performance just after manufacture.

The invention is further described in the following non-limiting examples.

EXAMPLE 1

Preparation of Modified Cottonseed Oil

A substantially peroxidized unsaturated oil is prepared from natural cottonseed oil. Natural cottonseed oil is added to a vessel having a steam jacket for heating. Steam is applied to the jacket to heat the oil to between 85 and 110° C. Air is bubbled through the oil while it is agitated. The flow rate of the air varies from about 1 standard cubic foot per hour (SCFH)/liter to 20 SCFH/liter. Agitation is such that the temperature of the oil remains constant over the time period of heating. The oil is heated for a time and at a temperature necessary to achieve a peroxide value as measured by the method of the US Pharmacopea (USP 24 NF 19 at page 1870) or by AOCS method 8-53 and then cooled, transferred to a different container and stored under nitrogen conditions. To achieve a peroxide value of about 10, at a temperature of about 89° C., the oil is heated for about 9 hours; at a temperature of about 100° C. the oil is heated for about 3 hours; at a temperature of about 105° C. the oil is heated for about 2.3 hours. To achieve a peroxide value of about 40, at a temperature of about 100° C., the oil is heated for about 6.75 hours, and at a temperature of about 105° C. the oil is heated for about 5.5 hours. To achieve a peroxide value of about 80, at a temperature of about 105° C. the oil is heated for about 8 hours. The relationship between the time and temperature of the oil as compared to its peroxide value is considered to be linear and one skilled in the art could achieve a desired peroxide value depending on the time and temperatures selected for processing.

EXAMPLE 2

Analysis of Release Properties

Figure 2:
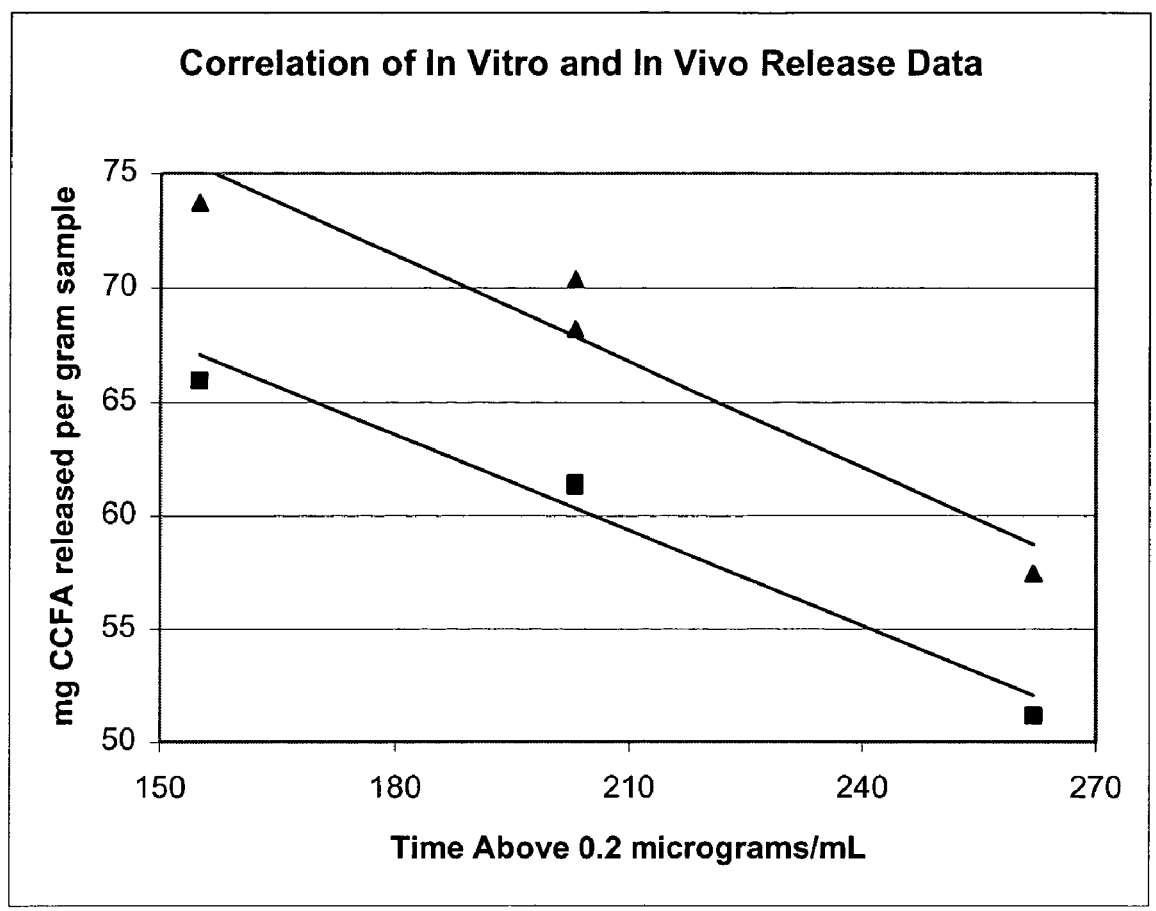
FIG. 2 is a graph showing the correlation of in vitro and in vivo release data.

In the following example, a procedure for determining the sustained release characteristics of a ceftiofur sustained-release composition is described. The procedure has been shown to correlate in vitro results with in vivo blood levels as illustrated in FIG. 2 wherein release of active component (ceftiofur) of the formulation is compared with blood levels in vivo.

In Vitro Testing of Inventive Compositions
 a) General Dissolution Procedure

| Equipment: | |
|---|---|
| Platform Shaker: | Reciprocating shaker model 5850 commercially available from Eberbach, nominal stroke length approximately 2.54 cm, frequency 200 cycles/minute. The vials were in a horizontal position and were aligned parallel to the stroke direction. Maintain platform shaker in a suitably controlled temperature environment (e.g. 22° C.). |
| Vials: | 40 mL (EPA type) Teflon lined screw cap. Commercially available from Qorpak (part number 7588T). |
| Plastic Syringes: | BD Disposable 10 mL plastic syringes or equivalent. |
| Filters: | Acrodisk 0.2 micron (part number 4496) |

The drug release experiments employed a 0.05 molar pH 6.5 phosphate buffer as a dissolution medium prepared by adding 31.98 grams of potassium phosphate monobasic and 15.39 grams potassium phosphate dibasic to deionized water and diluting to 1000 mL, then diluting again by a factor of 10 with deionized water (i.e. 100 mL of stock buffer to 1000 mL with deionized water).

b) Procedure:

Dispense an appropriate amount (e.g. 30-70 mg) of the composition for dissolution testing into an empty 40 mL vial. Equilibrate at appropriate temperature (e.g. 22° C.). Equilibrate the dissolution medium at an appropriate temperature (e.g. 22° C.). Add an appropriate volume (e.g. 30 mL) of dissolution medium into the vial containing the sample for dissolution testing. Repeat for all samples. Complete this process within about 2-3 minutes. Start agitation.

At predetermined time points, (e.g. 30 minutes or 60 minutes) remove samples for quantitative analysis. Filter if necessary. Proceed to quantitative analysis.

c) General Quantitative Analytical Procedure

Unless otherwise mentioned the following general procedure was followed.

| | |
|---|---|
| Apparatus: | HPLC capable of isocratic operation (e.g. Agilent 1100 commercially available from Agilent Technologies). |
| Detector: | UV-Vis Detector at 254 nm (e.g. Diode array detector, detection wavelength: 254 nm, commercially available from Agilent Technologies). |
| Column: | Waters Symmetry C8, 3.9 × 50 mm, commercially available from Waters Corporation. |
| Injection volume: | 10 μl |
| Flow rate: | 1-2 ml/min |
| Pressure: | 3000 psi |
| Mobile phase: | 3.85 g ammonium acetate, 13.5 ml of 40% tetrabutylammonium hydroxide were dissolved in Milli-Q water to give a total volume of 700 ml. The pH was adjusted to 6.7 ± 0.1 with glacial acetic acid. Then the solution was filtered through a 0.45 μm membrane filter. After filtration 200 ml methanol and 110 ml tetrahydrofuran were added and the mixture was sonicated under vacuum to degas it. | d) Calculation of the Released Amount of Analyte

The amount of released analyte (e.g. Ceftiofur) at each point in time can be calculated according to the following formula.

$$\frac{\text{mg Analyte released}}{\text{gram composition}} = \frac{(Wstd * P)}{Rstd} * \frac{DISVOL}{WSVOL} * \frac{Rsam}{Wsam} * \frac{1000}{1}$$

where,
 Wstd=Weight of the standard preparation, in mg
 P=Purity of the reference standard as Ceftiofur Free Acid
 Rstd=Peak area of Standard Preparation
 DISVOL=Volume of dissolution fluid, in mL (30)
 WSVOL=Volume of working standard, in mL (10)

Rsam=Peak area of Sample Preparation
Wsam=Weight of sample suspension in mg
1000=Conversion of sample weight from mg to gram In Vivo Testing of Inventive Compositions Cows suffering from either bovine respiratory disease or an anaerobic infection of the interdigital space are injected with any of the compositions of Examples 1-8 such that the level of administration of CCFA is between about 4.4 to about 6.6 mg CCFA/kg animal body weight. Administration is by subcutaneous injection in the neck or subcutaneous injection in the ear as described in U.S. Pat. No. 6,074,657. The concentration of effective CCFA metabolites in the blood plasma of the cows rises to at least 0.2 μg/ml within one hour of administration and remains at or above this level for at least 80 to about 140 hours. Only one administration of CCFA is required for the treatment regimen.

Correlation of In Vitro and In Vivo Sustained Release

Three lots of ceftiofur free acid suspension that exhibited different in vivo pharmacokinetic performance were used in evaluating in vivo release with the in vitro procedure. The lots exhibited different in vivo pharmacokinetic performance. The differences in pharmacokinetic performance were evidenced by differences in the duration of the sustained release effect, which is given by the number of hours which ceftiofur was detected in the blood stream of the animals commonly referred to as "time above 0.2 mcg/mL". The correlation of in vitro drug release results with time above 0.2 mcg/mL is shown in FIG. 2. In vitro results are given for samples taken at 60 minute (data points represented by squares) and 150 minute (data points represented by triangles) time points. The solid lines are the best least squares fit for the data and are included to illustrate the inverse correlation between amount released, in vitro, and the duration of the sustained release effect observed in vivo. Lots that released more CCFA at a given time in vitro had shorter duration of sustained release in vivo. As can be seen from FIG. 2, compositions demonstrating a release rate in the in vitro assay of between 50 and 70 mg per gram of composition per 60 minutes provide an in vivo sustained release for greater than 150 hours.

EXAMPLE 3

Manufacturing of 100 mg/mL CCFA Formulation in Vehicle Containing 0.01% (0.0001 Parts) and Cottonseed Oil (CSO) in 99.99% (0.9999 Parts) Miglyol 812

(i) To 0.0001 parts (0.3 mL) by volume CSO was mixed with 0.9999 parts (2999.7 mL) by volume Miglyol 812 for form a carrier vehicle.
(ii) 0.111 parts by weight of CCFA were added and mixed to form a uniform suspension such that the resulting concentration of CCFA was 100 mg/mL.
(iii) The suspension was heated at 95° C. for 22.9 hours.
(iv) The suspension was packaged and sterilized by gamma irradiation.

The resulting product is a stable, sustained-release formulation of CCFA having a concentration of 100 mg/mL and an in vitro sustained release of 52.6 mg/gm.

EXAMPLE 4

Manufacturing of 100 mg/mL CCFA Formulation in Vehicle Containing 0.001% (0.00001 Parts) Cottonseed Oil (CSO) and 99.999% (0.99999 Parts) Miglyol 812

(i) To 0.00001 parts (0.03 mL) by volume CSO was mixed with 0.99999 parts (2999.97 mL) by volume Miglyol 812 for form a carrier vehicle.
(ii) 0.111 parts by weight of CCFA were added and mixed to form a uniform suspension such that the resulting concentration of CCFA was 100 mg/mL.
(iii) The suspension was heated at 95° C. for up to 22.6 hours.
(iv) The suspension was packaged and sterilized by gamma irradiation.

The resulting product is a stable, sustained-release formulation of CCFA having a concentration of 100 mg/mL and sustained release as determined by in vitro testing of 52.0 mg/gm.

EXAMPLE 5

Manufacturing of 100 mg/mL CCFA Formulation in Vehicle Containing 0.0001% (0.000001 Parts) Cottonseed Oil (CSO) and 99.9999% (0.999999 Parts) Miglyol 812

(i) To 0.000001 parts (0.003 mL) by volume CSO was mixed with 0.999999 (2999.997 mL) parts by volume Miglyol 812 for form a carrier vehicle.
(ii) 0.111 parts by weight of CCFA were added and mixed to form a uniform suspension such that the resulting concentration of CCFA was 100 mg/mL.
(iii) The suspension was heated at 95° C. for up to 23.0 hours.
(iv) The suspension was packaged and sterilized by gamma irradiation.

The resulting product is a stable, sustained-release formulation of CCFA having a concentration of 100 mg/mL and sustained release as determined by in vitro testing of 52.0 mg/gm.

EXAMPLE 6

Manufacturing of 200 mg/mL CCFA Formulation Containing 0.00000048 Parts) Trilinolein and 0.99999952 Parts Miglyol 812

(i) To 0.00000048 parts (0.0009 mL) by volume of trilinolein are mixed with 0.99999952 parts (1874.9991 mL) by volume of Miglyol 812 to form a carrier vehicle.
(ii) 0.22 parts by weight of CCFA are added and mixed for 1 hour to form uniform suspension such that the concentration of CCFA is 200 mg/mL.
(iii) The suspension is heated to about 85-110° C. and permitted to cool.
(iv) The suspension is packaged and sterilized with gamma radiation.

The resulting product is a stable, sustained-release formulation of CCFA having a concentration of 200 mg/mL.

Having described the invention in detail and by reference to the preferred embodiments thereof, it will be apparent that modifications and variations are possible without departing from the scope of the appended claims.

The invention claimed is:

1. A composition comprising;
   (a) crystalline ceftiofur free acid; and
   (b) a vehicle comprising;
      (i) a modified liquid carrier having a peroxide value of between about 10 to about 600 milliequivalents (mEq) of peroxide per 1000 grams of oil, and
      (ii) an un-modified liquid carrier wherein the ratio by volume of the modified liquid carrier to the un-modified liquid carrier is between 0.00001:99.99999 to less than 0.01:99.99.

2. The composition according to claim 1 wherein said vehicle comprises a modified liquid carrier and an un-modified, unsaturated oil suitable for modification.

3. The composition according to claim 1 wherein said vehicle comprises a modified and an un-oxidizable oil.

4. The composition according to claim 1 wherein said modified liquid carrier comprises a modified vegetable oil wherein said vegetable oil is selected from the group consisting of corn oil, peanut oil, sesame oil, olive oil, palm oil, safflower oil, soybean oil, cottonseed oil, rapeseed oil, sunflower oil and mixtures thereof.

5. The composition according to claim 2 wherein said modified liquid carrier comprises modified cottonseed oil.

6. The composition according to claim 2 wherein said un-modified liquid carrier comprises coconut oil.

7. The composition according to claim 5 wherein the concentration of crystalline ceftiofur free acid in said composition ranges from 50 mg/ml to 250 mg/ml.

8. The composition according to claim 5 wherein the concentration of crystalline ceftiofur free acid in said composition ranges from about 100 mg/ml to about 200 mg/ml.

9. The composition according to claim 6 wherein the concentration of crystalline ceftiofur free acid in said composition ranges from 50 mg/ml to 250 mg/ml.

10. The composition according to claim 6 wherein the concentration of crystalline ceftiofur free acid in said composition ranges from about 100 mg/ml to about 200 mg/ml.

* * * * *